United States Patent [19]

Blind et al.

[11] 4,024,127

[45] May 17, 1977

[54] PROCESS FOR THE PREPARATION OF 5-ALKYL-10-AMINO-DIHYDRODIBEN-ZOAZEPINES

[75] Inventors: André Blind; Hubert Linares, both of Rhone, France

[73] Assignee: Rhone-Poulenc S.A., Paris, France

[22] Filed: Sept. 11, 1973

[21] Appl. No.: 396,143

[30] Foreign Application Priority Data

Sept. 12, 1972 France .............................. 72.32287

[52] U.S. Cl. ...................... 260/239 D; 260/465 E; 424/244
[51] Int. Cl.² ...................................... C07D 223/22
[58] Field of Search ................................ 260/239 D

[56] References Cited
UNITED STATES PATENTS 3,622,565  11/1971  Fouche et al. ................. 260/239 D

FOREIGN PATENTS OR APPLICATIONS 46-9340  9/1971  Japan ................................. 260/239

OTHER PUBLICATIONS

Reynolds et al., J. Org. Chem., vol. 16, p. 165 (1951).
Smith; A. S., "The Chemistry of Open–Chain Organic Nitrogen Compounds", vol. I, pp. 66 and 211 (1965).

Primary Examiner—Donald G. Daus
Assistant Examiner—D. B. Springer
Attorney, Agent, or Firm—Stevens, Davis, Miller & Mosher

[57] ABSTRACT

5-Alkyl-10-amino-10,11-dihydrodibenzo[b,f]azepines, useful as starting materials for the preparation of agricultural fungicides and also as therapeutic agents, are obtained by the reaction in an inert organic solvent of an N-alkyl-N-o-tolylanthranilonitrile with an alkali metal amide prepared from an amine, and the imino radical in the resulting 10-imino-10,11-dihydrodibenzo[b,f]azepine is converted to the amino radical by catalytic hydrogenation.

11 Claims, No Drawings

PROCESS FOR THE PREPARATION OF 5-ALKYL-10-AMINO-DIHYDRODIBENZOAZEPINES

This invention relates to a new process for the preparation of 5-alkyl-10-amino-10,11-dihydrodibenzo[b,f]azepines of the general formula:

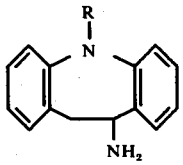

wherein R represents an alkyl radical containing 1 to 5 carbon atoms.

The compounds of general formula I are known to be useful intermediates in organic syntheses: in particular, they are useful as starting materials for the preparation of 10,11-dihydrodibenzo[b,f]azepine derivatives described in the specification of British Pat. No. 1,253,486 [granted to Rhone-Poulenc S.A. on an application filed June 22, 1970] as agricultural fungicides. They are also useful in their own right as therapeutic agents (cf. the specification of British Pat. No. 1,180,164 granted to Rhone-Poulenc S.A. on an application filed Jan. 18, 1968).

Hitherto, the compounds of general formula I have been prepared by a multi-stage process involving, as intermediates, ketones of the general formula:

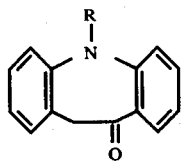

(wherein R is as hereinbefore defined), themselves obtained by hydrolysis of corresponding 5-alkyl-10-methoxy-dibenzo[b,f]azepines, as described in British patent specifications Nos. 1,253,486 and 1,180,164. The ketones of general formula II are first converted into the corresponding oximes and then the latter are reduced to amines by catalytic hydrogenation or by the action of sodium in a saturated primary alcohol, or by sodium amalgam.

It has now been found that the compounds of general formula I can be prepared by a process which is simpler and more rapid than the previously known method and which utilises anthranilonitriles of the general formula:

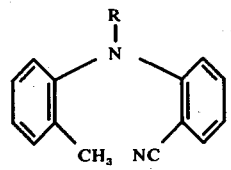

wherein R is as hereinbefore defined.

According to the present invention, a new process for the preparation of the compounds of general formula I comprises reacting an N-alkyl-N-o-tolylanthranilonitrile of general formula III with an alkali metal amide prepared from an amine in an inert organic solvent, and converting the imino radical in the resulting 10-imino-10,11-dihydrodibenzo[b,f]azepine of the general formula:

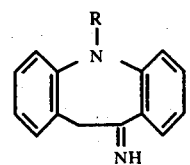

(wherein R is as hereinbefore defined) to the amino radical by catalytic hydrogenation, optionally in situ.

The cyclisation of the anthranilonitriles of general formula III to the dihydrodibenzoazepines of general formula IV is carried out by the action of an alkali metal amide such as a potassium, sodium or lithium amide, which is prepared according to known processes, e.g. by reacting an amine directly with the alkali metal or with an organo-metallic compound such as phenyl-lithium, naphthyl-lithium or napthyl-sodium. Sodium or lithium amides prepared with secondary amines such as piperidine, dimethylamine, diethylamine and N-methylaniline are particularly suitable. The amount of amide employed is at least one mol per mol of nitrile treated. The inert organic solvent used is advantageously a polar aprotic solvent which is inert under the reaction conditions, such as tetrahydrofuran, dimethylformamide, 1,2-dimethoxyethane or dioxan. It is also possible to use hexamethylphosphotriamide as the solvent, either alone or mixed with one of the above-mentioned polar aprotic solvents or with an aliphatic or aromatic hydrocarbon such as hexane, benzene or toluene. When the amine used to prepare the amide is liquid such as, for example, piperidine, the reaction involving cyclisation of the nitriles of general formula III is conveniently carried out in an excess of the said amine; in this case, the alkali metal amide is prepared in an excess of amine and the nitrile of general formula III is then added.

The reaction of the anthranilonitrile of general formula III with the amide is carried out at temperatures between −25° and +50° C., and preferably between +20° and +40° C.

The cyclisation product of general formula IV is not generally isolated and catalytic hydrogenation of it, which constitutes the second stage of the process, can be carried out directly on the reaction mixture. The hydrogenation is effected in the presence of the usual hydrogenation catalysts employed for the conversion of an imino radical to an amino radical such as palladium, platinum, rhodium, ruthenium, nickel or, preferably, Raney nickel, at a temperature of from 20° to 150° C. and under a hydrogenation pressure which can be as much as 150 bars. The amine of general formula I resulting from this hydrogenation is then isolated and purified, optionally through the intermediary of a salt thereof.

The N-alkyl-N-o-tolylanthranilonitriles of general formula III are new compounds and as such form another feature of the invention. They can be prepared by alkylation of N-o-tolylanthranilonitrile by methods known per se for the alkylation of amines, for example, by means of an alkyl halide or a dialkyl sulphate, in the presence of an alkaline inorganic agent, in an inert solvent. By the term "methods known per se" as used in this specification is meant methods heretofore used or described in the chemical literature.

N-o-Tolylanthranilonitrile can itself be prepared by using the corresponding amide as an intermediate in accordance with the process described in the specification of British Pat. No. 1,121,447 [granted to Bristol-Myers Company on an application filed April 12, 1966], or by reacting N-o-tolylanthranilic acid with a primary organosilylamine in the presence of a Lewis acid, in accordance with the process described in the specification of German Patent Application No. 2205360 filed by Rhone-Poulenc S.A. on Feb. 4, 1972.

The following Examples illustrate the invention.

EXAMPLE 1

Naphthalene (5.7 g.), anhydrous tetrahydrofuran (70 cc.) and lithium granules (0.630 g.) are introduced under a nitrogen atmosphere into a 500 cc. flask and cooled to 0° C. A solution of dimethylamine (4.80 g.) in tetrahydrofuran (100 cc.) is then run in and the mixture left at 0° C. for 1 hour. The temperature is then raised to 30° C. and a solution of N-methyl-N-o-tolylanthranilonitrile (9.90 g.) in tetrahydrofuran (20 cc.) is run in. After 1 hour, the mixture is cooled to about 3° C. on an ice/acetone bath and anhydrous ethanol (10 cc.) is added slowly to it.

The reaction mixture, of a greenish yellow colour, is transferred into an autoclave cooled to 0° C., which has been flushed with a stream of nitrogen and which contains Raney nickel (1 g.) suspended in tetrahydrofuran (50 cc.). The mixture is saturated with a stream of ammonia, a hydrogen pressure of 50 bars is established in the autoclave and the mixture is heated at 90° C. for 2 hours. After cooling and purging of the autoclave with nitrogen, water (3 cc.) is added. The reaction mixture is then decanted, heated under reflux for 45 minutes, and the precipitate filtered off and rinsed on the filter with hot tetrahydrofuran (2 × 15 cc.). The filtrate is cooled in an ice-bath and a 10N aqueous solution of hydrochloric acid is added slowly until the pH is 5-6 and the mixture is left for a further 30 minutes in the ice-bath. A solid product is filtered off, rinsed with tetrahydrofuran (4 × 20 cc.) and dried under reduced pressure (20 mm.Hg) to give 5-methyl-10-amino-10,11-dihydrodibenzo[b,f]azepine hydrochloride (10.07 g.), which melts with decomposition at about 270° C. Yield 86.8%.

N-Methyl-N-o-tolylanthranilonitrile used as starting material can be prepared in the following way:

a. N-o-Tolylanthranilic acid (56.8 g.), hexamethyldisilazane (92.5 g.) and aluminium chloride (0.75 g.) are introduced into a 500 cc. autoclave. After having purged the autoclave with nitrogen, the mixture is heated under the autogenic pressure for 2 hours at 260° C. After cooling, the reaction mixture is extracted with diethyl ether (1,000 cc.) and the ether layer is washed with a 10% aqueous solution of sodium carbonate (4 × 100 cc.) and then with water until neutral. The mixture is dried over sodium sulphate and filtered and then the ether is evaporated from the filtrate. A solid product of a brown colour is obtained and is recrystallised from hexane (100 cc.). A white powder (44.1 g.), which melts at 74° C., is thus isolated and is identified by infra-red analysis and nuclear magnetic resonance as being N-o-tolylanthranilonitrile. Yield 85%.

b. N-o-Tolylanthranilonitrile (20.8 g.) and acetone (160 cc.) are introduced into a flask equipped with a reflux condenser and a dropping funnel and then heated at 40° C. Potassium hydroxide powder (9.34 g.; in the form of potash containing 80% of potassium hydroxide) is added slowly. The solution, which is coloured red, is stirred at 40° C. for 20 minutes. A solution of dimethyl sulphate (13.5 g.) in acetone (40 cc.) is then run in over the course of 36 minutes and stirring is continued at 40° C. for 2 hours. The acetone is distilled off and the residue is taken up in water (250 cc.) and then extracted with diethyl ether (3 × 80 cc.). The combined ether layers are washed with water (4 × 30 cc.), dried over sodium sulphate and filtered. On concentration of the filtrate, a solid residue (24.2 g.) is obtained, the recrystallisation of which from cyclohexane (50 cc.) yields a white solid product (19.8 g.) which melts at 68° C. and is identified by infra-red analysis, nuclear magnetic resonance and microanalysis as being N-methyl-N-o-tolylanthranilonitrile. Yield 89%.

EXAMPLE 2

The procedure of Example 1 is followed, but the lithium metal is replaced by sodium (2.05 g.). The reaction of the sodamide with the nitrile is carried out at 40° C. for 1 hour. The hydrogenation of Raney nickel is carried out under the same conditions as in Example 1 and at the end of the operation 5-methyl-10-amino-10,11-dihydrodibenzo[b,f]azepine hydrochloride (8.2 g.) is obtained.

EXAMPLE 3

Finely divided sodium metal (1 g.) is added to piperidine (160 cc.) and the mixture is heated under reflux (106° C.) until dissolution. The mixture is then cooled to 0° C., and a solution of N-methyl-N-o-tolylanthranilonitrile (2.76 g.) in piperidine (28 cc.) is added. The reaction mixture is stirred for 1 hour, its temperature being kept at 0° C. The temperature is then allowed to rise to 40° C. and the mixture is maintained at this temperature for 1 hour. Piperidine (168 cc.) is then distilled off under reduced pressure (20 mm.Hg). The residue, taken up in ethanol (80 cc.), is poured into an autoclave purged with nitrogen, and then saturated with ammonia. Raney nickel (1 g.) is added and a pressure of 30 bars of hydrogen is established in the autoclave. The mixture is then heated for 1 hour at 90°-100° C. After cooling and purging the autoclave with nitrogen, the reaction mixture is taken up in diethyl ether (150 cc.) and the ether phase is then washed successively with water (50 cc.), a saturated aqueous solution of sodium sulphate (2 × 50 cc.) and a saturated aqueous solution of sodium chloride (4 × 50 cc.). The ether layer is then extracted with methanesulphonic acid (2 × 15 cc. followed by 10 cc.) and washed with water (15 cc.). The aqueous layer thus obtained is immediately rendered alkaline by addition of a 10N aqueous solution of sodium hydroxide. The mixture is extracted with diethyl ether (3 × 70 cc.), washed with water and dried over potassium carbonate. On evaporation of the diethyl ether in vacuo, an oily product (2.63 g.) is obtained and is purified by passing it through a column of basic alumina (washing of the column with a 50/50 mixture by volume of petroleum ether and benzene and elution of the product by ethyl acetate). After evaporation of the eluate, a product (1.48 g.) is obtained which is washed with petroleum ether and dried. This product then has a melting point of 90°-92° C. It is identified as being 5-methyl-10-amino-10,11-dihydrodibenzo[b,f]azepine.

EXAMPLE 4

Lithium (0.11 g.) is added to piperidine (60 cc.) containing naphthalene (2.01 g.) and the mixture is stirred at about 20° C. until dissolution. N-Methyl-N-o-tolylanthranilonitrile (1.73 g.) dissolved in piperidine (17 cc.) is then added to this solution (duration of the running in process: 13 minutes) and the reaction mixture stirred at ambient temperature until the nitrile employed has been completely converted. After thin layer chromatography (solvent: cyclohexane/ethyl acetate; 4/1 by volume), the piperidine is distilled off and the residue subjected to a hydrogenation treatment similar to that of Example 3 and the reaction mixture is subsequently treated in the same way in order to isolate 5-methyl-10-amino-10,11-dihydrodibenzo[b,f]azepine.

We claim:
1. Process for the preparation of a 5-alkyl-10-amino-10,11-dihydrodibenzo[b,f]azepine of the formula:

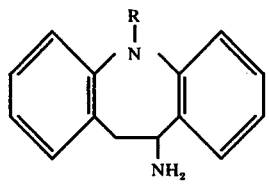

(wherein R represents alkyl of 1 through 5 carbon atoms) which comprises reacting an N-alkyl-N-o-tolylanthranilonitrile of the formula:

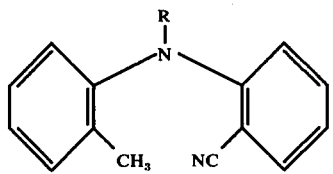

(wherein R is as hereinbefore defined) with an alkali metal amide of a secondary amine, in a proportion of at least one mole of said amide per mole of the said nitrile, said reaction being carried out in an inert organic solvent, and converting the imino radical in the resulting 10-imino-10,11-dihydrodibenzo[b,f]azepine of the formula:

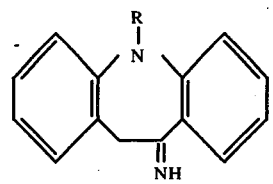

(wherein R is as hereinbefore defined) to the amino radical by catalytic hydrogenation.

2. Process according to claim 1 in which the alkali metal amide is a lithium amide or a sodium amide.

3. Process according to claim 1 in which the inert organic solvent is a polar aprotic solvent.

4. Process according to claim 1 in which the N-alkyl-N-o-tolylanthranilonitrile is N-methyl-N-o-tolylanthranilonitrile.

5. Process according to claim 1 in which the alkali metal amide is one prepared by reacting piperidine, dimethylamine, diethylamine, or N-methylaniline with phenyl-lithium naphthyl-lithium, or naphthyl-sodium.

6. Process according to claim 5 in which the inert organic solvent is the amine used in the preparation of the alkali metal amide.

7. Process according to claim 6 in which the inert organic solvent is piperidine.

8. Process according to claim 1 in which the reaction between the anthranilonitrile and alkali metal amide is carried out at a temperature between −25° and +50° C.

9. Process according to claim 8 in which the temperature is between +20° and +40° C.

10. Process according to claim 1 in which the catalytic hydrogenation of the 10-imino-10,11-dihydrodibenzo[b,f]azepine is carried out at a temperature of from 20° to 150° C. and under a hydrogen pressure of up to 150 bars.

11. Process according to claim 10 in which the catalytic hydrogenation of the 10-imino-10,11-dihydrodibenzo[b,f]azepine is carried out using Raney nickel as catalyst.

* * * * *